United States Patent
Leusch et al.

(12)

(10) Patent No.: US 6,238,648 B1
(45) Date of Patent: *May 29, 2001

(54) ANTI-CARIES ORAL CARE COMPOSITIONS AND THEIR METHODS OF USE

(75) Inventors: Mark Steven Leusch, Mason; Colleen Mary McSwiggin, Cincinnati; Phillip Asa Drake, Mason, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,344

(22) Filed: Mar. 25, 1999

(51) Int. Cl.[7] .................................... A61K 7/16
(52) U.S. Cl. ........................................... 424/49
(58) Field of Search ........................... 427/49–58

(56) References Cited

U.S. PATENT DOCUMENTS

| | | | |
|---|---|---|---|
| 3,914,434 | * 10/1975 | Bohni | 424/343 |
| 3,932,604 | * 1/1976 | Barth | 424/49 |
| 3,970,747 | * 7/1976 | Barth | 424/52 |
| 4,254,101 | * 3/1981 | Denny | 424/52 |
| 4,314,990 | * 2/1982 | Denny | 424/52 |
| 4,340,583 | * 7/1982 | Wason | 424/52 |
| 4,457,921 | * 7/1984 | Stroz et al. | 424/180 |
| 4,508,713 | * 4/1985 | Stroz et al. | 514/60 |
| 4,556,553 | * 12/1985 | Susanuma et al. | 424/52 |
| 4,581,228 | * 4/1986 | Susanuma et al. | 424/52 |
| 4,587,119 | * 5/1986 | Bucke et al. | 424/48 |
| 4,950,479 | * 8/1990 | Hill et al. | 424/49 |
| 4,952,407 | 8/1990 | Record et al. | 424/440 |
| 5,089,255 | * 2/1992 | Gaffar et al. | 424/52 |
| 5,178,869 | * 1/1993 | Ebine et al. | 424/401 |
| 5,376,360 | * 12/1994 | Domke et al. | 424/52 |
| 5,424,059 | * 6/1995 | Prencipe et al. | 424/52 |
| 5,496,541 | * 3/1996 | Cutler | 424/50 |
| 5,531,982 | * 7/1996 | Gaffar et al. | 424/49 |
| 5,776,437 | * 7/1998 | Burgess et al. | 424/53 |
| 5,800,803 | 9/1998 | Mirajkar et al. | 424/54 |
| 5,804,165 | 9/1998 | Arnold | 424/44 |
| 5,811,080 | * 9/1998 | Burgess et al. | 424/53 |
| 5,820,852 | * 10/1998 | Burgess et al. | 424/52 |
| 5,820,853 | * 10/1998 | Glandorf | 424/52 |
| 5,820,854 | * 10/1998 | Glandorf | 424/52 |
| 5,849,269 | * 12/1998 | Burgess et al. | 424/52 |
| 5,885,553 | * 3/1999 | Michael | 424/49 |
| 5,900,230 | * 5/1999 | Cutler | 424/49 |
| 5,939,052 | * 8/1999 | White et al. | 424/52 |

FOREIGN PATENT DOCUMENTS

| | | | |
|---|---|---|---|
| 0009325 | 4/1980 | (EP) | A61K/7/16 |
| 0251146 | 1/1988 | (EP) | A61K/7/18 |
| 0413427A2 | 2/1991 | (EP) | A23G/3/30 |
| 0696449A2 | 2/1996 | (EP) | A61K/7/16 |
| 0800823A1 | 10/1997 | (EP) | A61K/31/045 |
| WO 92/06943 | 4/1992 | (WO) | C07C/31/18 |
| WO 00/15236 | 3/2000 | (WO) | A61K/31/70 |

OTHER PUBLICATIONS

Makinen et al., "Relationship Between Carbohydrate Sweeteners and Oral Diseases", *Prog. In Food and Nutrition Sci.*, 12 (1988) pp. 73–109.

Darwish et al., "Effect of Ethanol, Propylene Glycol and Glycerol on the Interaction of Methyl and Propyl P–hydroxybenzoate with *Staphylococcus Aureus* and *Pseudomonas Aeruginosa*", *International J. of Pharmaceutics*, 147 (1997) pp. 51–60.

Trahan, "Xylitol: A Review of Its Actions on *Mutans Streptococci* and Dental Plaque—Its Clinical Significance", *International Dental J.*, 45 (1995) pp. 77–92.

Birkhed et al., "Microbiological Aspects of Some Caloric Sugar Substitutes", *International Dental J.*, 35 (1985) pp. 9–17.

Makinen, "Latest Dental Studies on Xylitol and Mechanism of Action of Xylitol in Caries Limitation", *Progress in Sweeteners*, Edited by T. H. Grenby, Elsevier Science Publishers, (1989) pp. 331–362.

Linke, "Sweeteners and Dental Health: The Influence of Sugar Substitutes on Oral Microorganisms", *Developments in Sweeteners—3*, Edited by T. H. Grenby, Elsevier Applied Science, (1987) pp. 151–188.

Park et al., "Acidogenicity of High–Intensity Sweeteners and Polyols", *Amer. J. of Dentistry*, 8 (1995) pp. 23–26.

Kawanabe et al., "Noncariogenicity of Erythritol as a Substrate", *Caries Res.*, 26 (1992) pp. 358–362.

Carlsson, "Potentials of the Oral Microflora to Utilize Sugar Substitutes as Energy Source", *Health and Sugar Substitutes*, In, Proc. ERGOB Conf., Geneva, Karger, Basil, (1978) pp. 205–210.

Assev et al., "Sorbitol Increases The Growth Inhibition of Xylitol on Strep. Mutans OMZ 176", *Acta Path. Microbiol. Immunol. Scand.*, Sect. B., 94, (1986) pp. 231–237.

Soderling et al., "Effect of Sorbitol, Xylitol, and Xylitol/Sorbitol Chewing Gums on Dental Plaque", *Caries Res.*, 23, (1989) pp. 378–384.

(List continued on next page.)

*Primary Examiner*—Shep K. Rose
(74) *Attorney, Agent, or Firm*—John M. Howell

(57) ABSTRACT

The present invention relates to oral care compositions, including therapeutic rinses, tooth pastes and gels comprising a combination of a non-cariogenic carbohydrate and polyalcohol. This invention further relates to a method for treating or preventing conditions in the mouth that favor formation of tooth caries.

5 Claims, No Drawings

OTHER PUBLICATIONS

Waler et al., "Xylitol 5–P Formation by Dental Plaque After 12 Weeks' Exposure to a Xylitol/Sorbitol Containing Chewing Gum", *Scand. J. Dent. Res.* 100, (1992) pp. 319–321.

Topitsoglou et al., "Effect of Chewing Gums Containing Xylitol, Sorbitol or a Mixture of Xylitol and sorbitol on Plaque Formation, pH Changes and Acid Production in Human Dental Plaque", *Caries Res.*, 17, (1983) pp. 369–378.

Wennerholm et al., "Effect of Xylitol and Sorbitol in Chewing–Gums on *Mutans Streptococci*, Plaque pH and Mineral Loss of Enamel", *Caries Res.*, 28, (1994) pp. 48–54.

Sasaki et al., "Inhibitory Effect of Xylitol on the Acid Production Activity From Sorbitol by *Streptococcus Mutans* and Human Dental Plaque", *Bull. Tokyo Dent. Coll.*, 28, No. 1, (1987) pp. 13–18.

Frostell, "Interaction Between Xylitol and Sorbitol in Plaque Metabolism", *Swed Dent. J.*, 8, (1984) pp. 137–146.

Rolla et al., "Effect of Aqueous Solutions of Sorbitol–Xylitol on Plaque Metabolism and on Growth of *Streptococcus Mutans*", *Scand. J. Dent. Res.*, 89 (1981) pp. 247–250.

Assev et al., "Are Sodium Lauryl Sulfate–containing Toothpastes Suitable Vehicles for Xylitol?", *Eur J. Oral Sci.*, 105, (1997) pp. 178–182.

* cited by examiner

ANTI-CARIES ORAL CARE COMPOSITIONS AND THEIR METHODS OF USE

TECHNICAL FIELD

The present invention relates to oral care compositions, including therapeutic rinses, tooth pastes and gels comprising a combination of a non-cariogenic carbohydrate and a polyalcohol. This invention further relates to a method for treating or preventing conditions in the mouth that favor formation of tooth caries.

BACKGROUND ART

Dental caries is a progressive condition in which loss of hydroxyapatite mineral reduces the structural integrity of the teeth. Current understanding of dental caries suggests a bacterial etiology which is interdependent upon dietary factors, host defense mechanisms and time. When each of these components are present, dental caries occur. In part, the ability to control dental caries depends upon the effectiveness of oral hygiene treatments including dentifrice and mouth rinse. It is widely acknowledged that caries prevention is dependent upon the compatibility of the components comprising the oral hygiene products. For example, ii is well established that caries are reduced by the addition of fluoride (e.g. sodium fluoride, stannous fluoride, etc.) to a highly compatible dentifrice system. It is also acknowledged that dietary habits, in particular, consumption of carbohydrates such as sucrose can have profound impact on the incidence of dental caries.

Production of acids resulting from plaque's carbohydrate consumption contributes to caries lesion formation. The addition of sweeteners such as sorbitol and, or xylitol to gums, candies and foods have been found to help reduce the incidence of dental caries via significant increases in plaque pH and measurable decreases in plaque *S. mutans* levels; see U.S. Pat. No. 5,804,165, Arnold, issued Jul. 24, 1996; herein incorporated by reference. The combination of a non-cariogenic sweetener and a suitable fluoride system could provide a potentially powerful approach to controlling dental caries. While caries control has been observed in studies evaluating the benefits of long-term consumption of non-carogenic carbohydrates, bacterial effects have not been consistently shown for all xylitol containing dentifrices.

Some polyalcohols such as glycerol or propylene glycol have been shown to increase antimicrobial activity of hydrophobic preservative compounds such as methyl and propyl p-hydroxybenzoate (parabens). U.S. Pat. No. 5,800,803, Mirajkar et al., issued Feb. 10, 1997, assigned to Colgate, discloses increased uptake of anti-microbials such as triclosan in formulations containing propylene glycol. It is believed that these polyalcohols increase activity via perterbation of the cellular membranes. The degree of membrane perterbation may be related to the hydrophobicity of the polyalcohol. Low molecular weight glycols such as propylene or butylene glycol have also been used as preservatives in both foods and pharmaceutical products. The preservative properties are thought to be manifested through the reduction of water activity. Polyalcohols have also been used as humectants in oral products including dentifrice.

SUMMARY OF THE INVENTION

The present invention relates to oral care compositions, including tooth pastes (including gels and gels for subgingival application), mouth rinses, mouth sprays, chewing gums, and lozenges as more fully described hereinafter. These compositions comprise:

(a) a safe and effective amount of a non-cariogenic carbohydrate; and
(b) a polyalcohol;

wherein said polyalcohol is used in a level sufficient to promote greater uptake of said non-cariogenic carbohydrate by plaque, thereby resulting in creating an environment that does not favor development of caries.

This invention further relates to a method for preventing and treating conditions in the mouth that favor formation of caries by the use of compositions as disclosed above.

DETAILED DESCRIPTION OF THE INVENTION

The present invention relates to compositions and methods of treating or preventing the formation of caries. The methods of treating and preventing caries includes applying compositions comprising a non-cariogenic carbohydrate and a polyalcohol wherein when used in the oral cavity promotes uptake of the non-cariogenic carbohydrate by plaque.

Production of acids resulting from plaque's carbohydrate consumption contributes to caries lesion formation. Significant increases in plaque pH and measurable decreases in plaque *S. mutans* levels have been observed in studies evaluating the benefits of long-term consumption of non-cariogenic carbohydrates such as xylitol containing foods or gums. However, such pH and bacterial effects have not been consistently shown for all non-cariogenic carbohydrate containing dentifrices perhaps as the result of relatively short brushing periods, insufficient non-cariogenic carbohydrate dose and/or inadequate non-cariogenic carbohydrate delivery. Although the amount of non-cariogenic carbohydrate present in dentifrice could be established analytically, such analysis would not demonstrate that plaque bacteria could uptake the non-cariogenic carbohydrate.

The present invention encompasses a dentifrice composition which when applied to the teeth contains a non-cariogenic carbohydrate and a polyalcohol that enhances uptake of the non-cariogenic carbohydrates such that acid produced through plaque metabolism of sugars is temporarily disrupted. When used as part of a regular oral hygiene program, this composition could result in fewer carious lesions on the teeth. This result means that non-cariogenic carbohydrates can be more efficiently delivered to plaque bacteria resulting in higher cellular concentrations during relatively short brushing times compared to formulations which do not contain this combination. The higher cellular concentrations of non-cariogenic carbohydrate in plaque bacteria means a longer periods of metabolic disruption. Cumulatively longer periods of metabolic disruption could lead to fewer carious lesions.

A. Non-Cariogenic Carbohydrates

As discussed above, compositions of the present invention comprise non-cariogenic carbohydrates that can disrupt caries formation. Said non-cariogenic carbohydrates are used in the composition of the present invention from about 1% to about 65%, preferably about 2.5% to about 20% and most preferably about 5% to about 10% by weight of the composition.

Non-cariogenic carbohydrates are known in the art. See the following articles, all herein incorporated by reference: Carlsson, J. *Potentials of the Oral Microflora to Utilize Sugar Substitutes as Energy Source,*. In, Proc. ERGOB Conference, Geneva, Karger, Basil, (1978) pp. 205–210; Makinen, K. K. *Latest Dental Studies on Xylitol and Mechanism of Action of Xylitol in Caries Limitation*, Progress in Sweeteners, Elsevier Science Publishers, Ltd., London, (1989) pp.331–362.; Makinen, K. K. and P. Isokangas, *Relationship Between Carbohydrate Sweeteners and Oral Diseases*, Progress in Food and Nutrition Science 12:73–109, (1988); Trahan, L., *Xylitol: a review of its action on mutans streptococci and dental plaque—its clinical significance*, International Dental Journal 45:77–92, (1995); Birkhed, D. et al., *Microbiological Aspects of Some Caloric Sugar Substitutes*, International Dental Journal, 35:9–17 (1985); Kawanabe J. et al, *Noncariogenicity of Erythritol as a Substrate*, Caries Research, 26:358–362, (1992); Park, K.K. et al.; *Acidogenicity of High-intensity Sweeteners and Polyols*, American Journal of Dentistry, 8:23–26, (1995); Linke, H. *Sweeteners and Dental Health: the Influence of Sugar Substitutes on Oral Microorganisms*, Developments in Sweeteners, Elsevier Applied Science, (1987).

The non-cariogenic carbohydrates are sugars selected from the group of monosaccharides and disaccharides corresponding to the following empirical formula:

$$_xH_yO_z$$

wherein when a monosaccharides, x is from about 4 to about 6, y is from about 10 to about 14 and z is from about 4 to about 6. When a disaccharides, x is about 12, y is about 22 and z is about 11. The preferred sugars corresponding to the structure above are selected from the group consisting of erythritol, xylitol, arabitol, ribitol, xylose, melibiose, palitinose and mixtures thereof. Most preferred is xylitol.

Xylitol is the pentahydric alcohol corresponding to the empirical formula $C_5H_{12}O_5$ and is a white crystalline powder having the molecular weight of about 152.15 and a melting point from about 61° C. to about 61.5° C. Xylitol's solubility in water is about 64.2 g/100 g and has a relative sweetness comparable to sucrose. Xylitol is available from a number of suppliers including Roquette of Lestrem, France as Xylisorb 700™, Cultor Food Science of Thomson, Ill. as Xylitol C™, and Towa Chemical Industry, a division of Mitsubishi International, Fuji, Japan.

B. Polyalcohols

The present invention additionally comprises a polyhydric alcohol or polyalcohols. Polyalcohols are used in the composition of the present invention from about 0.1% to about 50%, preferably about 1% to about 25% and most preferably about 5% to 10% by weight of the composition. Preferred polyalcohols used in the present invention are selected from the group consisting of glycerin, sorbitol, polysorbates, xylitol, butylene glycols, polyethylene glycols, propylene glycol, triethanolamine, hexylene glycol and mixtures thereof. The most preferred are polyalcohols selected from the group consisting of propylene glycol, butylene glycol, polyethylene glycol and mixtures thereof. Most preferred is propylene glycol.

Propylene glycol is the aliphatic alcohol that corresponds to the empirical formula $C_3H_8O_2$ Propylene glycol is a clear, colorless liquid, substantially free of visible foreign material. Said material is practically odorless and is used in a number of cosmetic and food products. Suppliers including Dow of Plaquemine, La., Huntsman Chemical, Port Neches, Tex., Eastman Chemicals, South Charleston, W.V., Olin Chemical, Brandenburg, Ky., and Acro Chemicals, Bayport, Tex.

C. Pharmaceutically-Acceptable Excipients

The present invention may take on the form of a oral care/health care products known in the art. For example in one embodiment of the present invention, the non-cariogenic carbohydrate and polyol are contained together in the dentifrice. The dentifrice is used in the normal manner on the teeth. An alternative embodiment is where the non-cariogenic carbohydrate and polyol are contained in two separate phases of the dentifrice package. These phases would remain separate until combined just prior to applying to the teeth with an implement such as a tooth brush. Another embodiment comprises a solution of polyol that is separate from the dentifrice containing the non-cariogenic carbohydrate. After dispensing the dentifrice onto the brush, the polyol is dispensed onto the dentifrice and then mixed through the process of application to the teeth.

As a consequence of the present invention's adaptability to forms and packaging, a number of pharmaceutically acceptable excipients may be used in addition to the non-cariogenic carbohydrate and polyol. Many of these excipients are those routinely known for use in the art. A fairly broad, but, non-complete list of these excipients is disclosed in U.S. Pat. No. 5,281,412, Lukacovic et al., issued Jan. 25, 1994, assigned to P&G; herein incorporated by reference.

By "pharmaceutically-acceptable excipient" or "pharmaceutically-acceptable oral carrier," as used herein, it is meant one or more compatible solid or liquid filler diluents or encapsulating substances which are suitable for topical, oral administration. By "compatible," as used herein, it is meant that the components of the composition are capable of being comingled without interaction in a manner which would substantially reduce the composition's stability and/or efficacy for treating or preventing caries according to the compositions and methods of the present invention.

The carriers or excipients of the present invention can include the usual and conventional components of tooth pastes (including gels and gels for subgingival application), mouth rinses, mouth sprays, chewing gums, and lozenges (including breath mints) as more fully described hereinafter.

The compositions of the present invention can be dual phase compositions or single phase compositions. Normally, each phase in these two phase compositions is in a separate container or in a single container with two chambers. Prior to use of dual phase composition by the consumer, the two phases are combined by co-extrusion of the two separate phases, preferably at a 1:1 volume to volume ratio, and the composition is preferably used immediately after preparation, i.e. within about 5 minutes.

The two phases, however, can be combined from about 1 minute to about 1 hour before use, or during the use of the composition. Dual phase containers are disclosed in U.S. Pat. No. 5,052,590, Ratcliff, issued Oct. 1, 1991 and U.S. Pat. No. 4,330,531, Alliger, issued May 18, 1982.

The choice of a carrier to be used is basically determined by the way the composition is to be introduced into the oral cavity. If a tooth paste (including tooth gels, etc.) is to be used, then a "tooth paste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.). If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al., which is incorporated herein by reference; if a chewing gum is to be used, then a "chewing gum carrier" is chosen, as disclosed in, e.g., U.S. Pat. No. 4,083,955, to Grabenstetter et al., which is incorporated herein by reference (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. No. 5,198,220, Damani, issued Mar. 30, 1993, P&G, U.S. Pat. No. 5,242, 910, Damani, issued Sep. 7, 1993, P&G, all of which are incorporated herein by reference. Carriers suitable for the preparation of compositions of the present invention are well known in the art. Their selection will depend on secondary considerations like taste, cost, and shelf stability, etc.

Preferred compositions of the subject invention are in the form of dentifrices, such as tooth pastes, tooth gels and tooth powders. Components of such tooth paste and tooth gels generally include one or more of the following: a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such tooth paste or tooth gel may also include one or more of the following: an anticaries agent (from about 0.05% to about 0.3% as fluoride ion), and an anti-calculus agent (from about 0.1% to about 13%). Tooth powders, of course, contain substantially all non-liquid components.

Other preferred compositions of the present invention are non-abrasive gels, including subgingival gels, which generally include a thickening agent (from about 0.1% to about 20%), a humectant (from about 0.1% to about 90%), a flavoring agent (from about 0.04% to about 2%), a sweetening agent (from about 0.1% to about 3%), a coloring agent (from about 0.01% to about 0.5%), water (from about 2% to about 45%), and may comprise an anticaries agent (from about 0.05% to about 0.3% as fluoride ion), and an anti-calculus agent (from about 0.1% to about 13%).

Other preferred compositions of the subject invention are mouth washes, including mouth sprays. Components of such mouth washes and mouth sprays typically include one or more of the following: water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of the following: an anticaries agent (from about 0.05% to about 0.3% as fluoride ion), and an anti-calculus agent (from about 0.1% to about 3%).

Other preferred compositions of the subject invention are dental solutions. Components of such dental solutions generally include one or more of the following: water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of the following: a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in U.S. Pat. No. 4,642, 903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 3,882, 228; U.S. Pat. No. 4,687,662; U.S. Pat. No. 4,642,903. All of these patents are incorporated herein by reference in their entirety.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, $19^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994, which is herein incorporated by reference in its entirety.

Types of carriers or oral care excipients which may be included in compositions of the present invention, along with specific non-limiting examples, are:

1. Abrasives

Dental abrasives useful in the topical, oral carriers of the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica I_. xerogels marketed under the trade name "Syloid" by the W.R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the tooth pastes of the present invention are described in more detail in Wason, U.S. Pat. No. 4,340,583, issued Jul. 29, 1982. The abrasive in the tooth paste compositions described herein is generally present at a level of from about 6% to about 70% by weight of the composition. Preferably, tooth pastes contain from about 10% to about 50% of abrasive, by weight of the composition.

A particularly preferred precipitated silica is the silica disclosed in U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, all of which are assigned to the Procter & Gamble Co. All of these patents are incorporated herein by reference in their entirety.

Mixtures of abrasives can be used. All of the above patents regarding dental abrasives are incorporated herein by reference. The total amount of abrasive in dentifrice compositions of the subject invention preferably range from about 6% to about 70% by weight; tooth pastes preferably contain from about 10% to about 50% of abrasives, by weight of the composition. Solution, mouth spray, mouthwash and non-abrasive gel compositions of the subject invention typically contain no abrasive.

2. Sudsing Agents (Surfactants)

Suitable sudsing agents are those which are reasonably stable and form foam throughout a wide pH range. Sudsing agents include nonionic, anionic, amphoteric, cationic, zwitterionic, synthetic detergents, and mixtures thereof. Many suitable nonionic and amphoteric surfactants are disclosed by U.S. Pat. No. 3,988,433 to Benedict; U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a.) Nonionic and amphoteric surfactants

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name "Tween"), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

b.) Anionic surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

3. Fluoride Ions

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. These patents are incorporated herein by reference in their entirety.

The present composition may contain from about 50 ppm to about 3500 ppm, and preferably from about 500 ppm to about 3000 ppm of free fluoride ions.

4. Thickening Agents

In preparing tooth paste or gels, it is necessary to add some thickening material to provide a desirable consistency of the composition. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopolt series. Particularly preferred carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. No. 5,198,220, Damani, issued Mar. 30, 1993, P&G, U.S. Pat. No. 5,242,910, Damani, issued Sep. 7, 1993, P&G, and U.S. Pat. No. 4,443,430, Mattei, issued Apr. 17, 1984, all of which are incorporated herein by reference.

Thickening agents in an amount from about 0.1% to about 15%, preferably from about 2% to about 10%, more preferably from about 4% to about 8%, by weight of the total tooth paste or gel composition, can be used. Higher concentrations can be used for chewing gums, lozenges (including breath mints), sachets, non-abrasive gels and subgingival gels.

5. Humectants

As discussed above, the polyalcohols of the present invention may also act as a humectant. Humectants serve to keep tooth paste compositions from hardening upon exposure to air, to give compositions a moist feel to the mouth, and, for particular humectants, to impart desirable sweetness of flavor to tooth paste compositions. Suitable humectants include glycerin, sorbitol, butylene glycol, polyethylene glycol, and especially sorbitol and glycerin.

6. Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

As in the case of the humectants, sweetening agents that can be used in the present invention may include the non-cariogenic carbohydrates disclosed above. Sweeteners useful in compositions of the present invention include sucrose, glucose, saccharin, dextrose, levulose, lactose, mannitol, sorbitol, fructose, maltose, xylitol, saccharin salts, thaumatin, aspartame, D-tyyptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety.

Preferred salivating agents of the present invention include Jambu® manufactured by Takasago. Preferred warming agents include capsicum and nicotinate esters, such as benzyl nicotinate. Preferred numbing agents include benzocaine, lidocaine, clove bud oil, and ethanol.

7. Anti-calculus Agent

The present invention also includes an anti-calculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

9. Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

10. Miscellaneous Carriers

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

Antimicrobial anti-plaque agents can also by optionally present in oral compositions. Such agents may include, but are not limited to, triclosan, 5-chloro-2-(2,4-dichlorophenoxy)-phenol, as described in *The Merck Index*, 11th ed. (1989), pp. 1529 (entry no. 9573) in U.S. Pat. No. 3,506,720, and in European Patent Application No. 0,251,591 of Beecham Group, PLC, published Jan. 7, 1988; chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpyridinium chloride (CPC) (*Merck Index*, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above antimicrobial antiplaque agents. If present, the antimicrobial antiplaque agents generally comprise from about 0.1% to about 5% by weight of the compositions of the present invention.

Anti-inflammatory agents may also be present in the oral compositions of the present invention. Such agents may include, but are not limited to, non-steroidal anti-inflamnnatory agents such as aspirin, ketorolac, flurbiprofen, ibuprofen, naproxen, indomethacin, aspirin, ketoprofen, piroxicam and meclofenarnic acid, and mixtures thereof. If present, the anti-inflammatory agents generally comprise from about 0.001% to about 5% by weight of the compositions of the present invention. Ketorolac is described in U.S. Pat. No. 5,626,838, issued May 6, 1997. Both of these references are incorporated herein by reference in their entirety.

Other optional agents include synthetic anionic polymeric polycarboxylates being employed in the form of their free acids or partially or preferably fully neutralized water soluble alkali metal (e.g. potassium and preferably sodium) or ammonium salts and are disclosed in U.S. Pat. No. 4,152,420 to Gaffar, U.S. Pat. No. 3,956,480 to Dichter et al., U.S. Pat. No. 4,138,477 to Gaffar, U.S. Pat. No. 4,183,914 to Gaffar et al., and U.S. Pat. No. 4,906,456 to Gaffar et al. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation.

The present invention can also optionally comprise selective H-2 antagonists including compounds disclosed in U.S. Pat. No. 5,294,433, Singer et al., issued Mar. 15, 1994, which is herein incorporated by reference in its entirety.

D Composition Use

A safe and effective amount of the compositions of the present invention may be topically applied to the mucosal tissue of the oral cavity, to the gingival tissue of the oral cavity, and/or to the surface of the teeth, for the treatment or prevention of the above mentioned diseases or conditions of the oral cavity, in several conventional ways. For example, the gingival or mucosal tissue may be rinsed with a solution (e.g., mouth rinse, mouth spray), a dentifrice (e.g., tooth paste, tooth gel or tooth powder), and the gingival/mucosal tissue or teeth are bathed in the liquid and/or lather generated by brushing the teeth. Other non-limiting examples include applying a non-abrasive gel or paste directly to the gingival/mucosal tissue or to the teeth with or without an oral care appliance described below; a chewing gum; or by chewing or sucking on a lozenge. Preferred methods of applying the composition to the gingival/mucosal tissue and/or the teeth are via rinsing with a mouth rinse solution and via brushing with a dentifrice. Other methods of topically applying the composition to the gingival/mucosal tissue and the surfaces of the teeth are apparent to those skilled in the art.

For the method of preventing and treating diseases or conditions of the oral cavity of the present invention, the composition is preferably applied to the gingival/mucosal tissue and/or the teeth (for example, by rinsing with a mouth rinse, directly applying a non-abrasive gel with or without a device, applying a dentifrice or a tooth gel with a toothbrush, sucking or chewing a lozenge preferably for at least about 10 seconds, preferably from about 20 seconds to about 10 minutes, more preferably from about 30 seconds to about 60 seconds). The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized, and the patient's response to treatment. If delivery to the periodontal pockets is desirable, such as with the treatment of periodontal disease, a mouth rinse can be delivered to the periodontal pocket using a syringe or water injection device. These devices are known to one skilled in the art. Devices of this type include "Water Pik" by Teledyne Corporation. After irrigating, the subject can swish the rinse in the mouth to also cover the dorsal tongue and other gingival and mucosal surfaces. In addition a tooth paste, non-abrasive gel, toothgel, etc. can be brushed onto the tongue surface and other gingival and mucosal tissues of the oral cavity.

The following non-limiting examples further describe preferred embodiments within the scope of the present invention. Many variations of these examples are possible without departing from the scope of the invention.

All percentages used herein are by weight of the composition unless otherwise indicated.

EXAMPLES

Example I

A dentifrice composition of the present invention contains the following components as described below:

| Item # | Material | % Comp. (w/w) |
|---|---|---|
| 1 | Glycerin | 14.0 |
| 2 | Polyethylene Glycol 300 | 4.5 |
| 3 | Silica | 21.5 |
| 4 | Tetrasodium Pyrophosphate | 4.5 |
| 5 | Water | 23.5 |
| 6 | Xanthan Gum | 0.3 |
| 7 | Carboxymethyl Cellulose | 0.5 |
| 8 | Sodium Fluoride | 0.2 |
| 9 | Flavor | 1.0 |
| 10 | Sodium Lauryl Sulfate (27.9% Solution) | 4.5 |
| 11 | Sodium Saccharin | 0.4 |
| 12 | Titanium Dioxide | 0.4 |
| 13 | Sodium Bicarbonate | 0.9 |
| 14 | Sodium Carbonate, Anhydrous | 1.4 |
| 15 | Poloxamer 407 | 1.8 |
| 16 | Xylitol | 10.0 |
| 17 | Propylene Glycol | 10.6 |
| | | Total 100.00 |

Method of Manufacture

The jacket temperature of a mixing tank is set to about 150° F. to about 160° F. Add humectants and water to the mixing tank and agitate. Upon the temperature reaching approximately 120° C., add the non-cariogenic carbohydrate (xylitol), fluoride, sweetening agents, coloring agents, titanium dioxide, and buffering agents. After mixing, add thickening agents to the abrasives. Upon becoming homogeneous, add the resulting mixture to the mixing tank with high agitation. Add the surfactant to the mixing tank and continue to mix until homogeneous. Cool the tank to about 120° F., adding the flavoring agents and tetrasodium pyrophosphates. Continue mixing for approximately 20 minutes.

Example II

A dentifrice composition of the present invention contains the following components as described below:

| Item # | Material | % Comp. (w/w) |
|---|---|---|
| 1 | Glycerin | 21.53 |
| 2 | Polyethylene Glycol 300 | 4.46 |
| 3 | Silica | 21.43 |
| 4 | Tetrasodium Pyrophosphate | 4.50 |
| 5 | Water | 23.54 |
| 6 | Xanthan Gum | 0.31 |
| 7 | Carboxymethyl Cellulose | 0.45 |
| 8 | Sodium Fluoride | 0.22 |
| 9 | Flavor | 0.98 |
| 10 | Sodium Lauryl Sulfate (27.9% Solution) | 4.46 |
| 11 | Sodium Saccharin | 0.36 |
| 12 | Titanium Dioxide | 0.45 |
| 13 | Sodium Bicarbonate | 0.89 |
| 14 | Sodium Carbonate, Anhydrous | 1.43 |
| 15 | Poloxamer 407 | 1.78 |
| 16 | Xylitol | 2.50 |
| 17 | Propylene Glycol | 10.71 |
| | | Total 100.00 |

Method of Manufacture

The method for making the above example is the method of manufacture of Example I.

Example III

A dentifrice composition of the present invention contains the following components as described below:

| Item # | Material | % Comp. (w/w) |
|---|---|---|
| 1 | Glycerin | 32.13 |
| 2 | Polyethylene Glycol 300 | 4.46 |
| 3 | Silica | 21.43 |
| 4 | Tetrasodium Pyrophosphate | 4.50 |
| 5 | Water | 23.54 |
| 6 | Xanthan Gum | 0.31 |
| 7 | Carboxymethyl Cellulose | 0.45 |
| 8 | Sodium Fluoride | 0.22 |
| 9 | Flavor | 0.98 |
| 10 | Sodium Lauryl Sulfate (27.9% Solution) | 4.46 |
| 11 | Sodium Saccharin | 0.36 |
| 12 | Titanium Dioxide | 0.45 |
| 13 | Sodium Bicarbonate | 0.89 |
| 14 | Sodium Carbonate, Anhydrous | 1.43 |
| 15 | Poloxamer 407 | 1.79 |
| 16 | Xylitol | 2.50 |
| 17 | Propylene Glycol | 0.10 |
| | | Total 100.00 |

Method of Manufacture

The method for making the above example is the method of manufacture of Example I.

Example IV

A dentifrice composition of the present invention contains the following components as described below:

| Item # | Material | % Comp. (w/w) |
|---|---|---|
| 1 | Glycerin | 6.88 |
| 2 | Polyethylene Glycol 300 | 5.00 |
| 3 | Silica | 21.50 |
| 4 | Tetrasodium Pyrophosphate | 4.50 |
| 5 | Water | 14.43 |
| 6 | Xanthan Gum | 0.35 |
| 7 | Carboxymethyl Cellulose | 0.50 |
| 8 | Sodium Fluoride | 0.24 |
| 9 | Flavor | 1.10 |
| 10 | Sodium Lauryl Sulfate (27.9% Solution) | 5.00 |
| 11 | Sodium Saccharin | 0.40 |
| 12 | Titanium Dioxide | 0.50 |
| 13 | Sodium Bicarbonate | 1.00 |
| 14 | Sodium Carbonate, Anhydrous | 1.60 |
| 15 | Poloxamer 407 | 2.00 |
| 16 | Xylitol | 10.00 |
| 17 | Propylene Glycol | 25.00 |
| | | Total 100.00 |

Method of Manufacture

The method for making the above example is the method of manufacture of Example I.

Example V

A dentifrice composition of the present invention contains the following components as described below:

| Item # | Material | % Comp. (w/w) |
|---|---|---|
| 1 | Glycerin | 9.12 |
| 2 | Polyethylene Glycol 300 | 5.00 |
| 3 | Silica | 21.50 |
| 4 | Tetrasodium Pyrophosphate | 4.50 |

-continued

| Item # | Material | % Comp. (w/w) |
|---|---|---|
| 5 | Water | 19.68 |
| 6 | Xanthan Gum | 0.35 |
| 7 | Carboxymethyl Cellulose | 0.50 |
| 8 | Sodium Fluoride | 0.25 |
| 9 | Flavor | 1.10 |
| 10 | Sodium Lauryl Sulfate (27.9% Solution) | 5.00 |
| 11 | Sodium Saccharin | 0.40 |
| 12 | Titanium Dioxide | 0.50 |
| 13 | Sodium Bicarbonate | 1.00 |
| 14 | Sodium Carbonate, Anhydrous | 1.60 |
| 15 | Poloxamer 407 | 2.00 |
| 16 | Arabitol | 2.50 |
| 17 | Butylene Glycol | 25.00 |
| | Total | 100.00 |

Method of Manufacture

The method for making the above example is the method of manufacture of Example I.

Example VI

A dentifrice composition of the present invention contains the following components as described below:

| Item # | Material | % Comp. (w/w) |
|---|---|---|
| 1 | Glycerin | 14.02 |
| 2 | Polyethylene Glycol 300 | 4.46 |
| 3 | Silica | 21.43 |
| 4 | Tetrasodium Pyrophosphate | 4.51 |
| 5 | Water | 23.54 |
| 6 | Xanthan Gum | 0.31 |
| 7 | Carboxymethyl Cellulose | 0.45 |
| 8 | Sodium Fluoride | 0.22 |
| 9 | Flavor | 0.98 |
| 10 | Sodium Lauryl Sulfate (27.9% Solution) | 4.46 |
| 11 | Sodium Saccharin | 0.36 |
| 12 | Titanium Dioxide | 0.45 |
| 13 | Sodium Bicarbonate | 0.89 |
| 14 | Sodium Carbonate, Anhydrous | 1.43 |
| 15 | Poloxamer 407 | 1.78 |
| 16 | Erythritol | 10.00 |
| 17 | Propylene Glycol | 10.71 |
| | Total | 100.00 |

Method of Manufacture

The method for making the above example is the method of manufacture of Example I.

Example VII

A dentifrice composition of the present invention contains the following components as described below:

| Item # | Material | % Comp. (w/w) |
|---|---|---|
| 1 | Glycerin | 21.52 |
| 2 | Polyethylene Glycol 300 | 4.46 |
| 3 | Silica | 21.43 |
| 4 | Tetrasodium Pyrophosphate | 4.50 |
| 5 | Water | 23.54 |
| 6 | Xanthan Gum | 0.31 |
| 7 | Carboxymethyl Cellulose | 0.45 |
| 8 | Sodium Fluoride | 0.22 |

-continued

| Item # | Material | % Comp. (w/w) |
|---|---|---|
| 9 | Flavor | 0.98 |
| 10 | Sodium Lauryl Sulfate (27.9% Solution) | 4.46 |
| 11 | Sodium Saccharin | 0.36 |
| 12 | Titanium Dioxide | 0.45 |
| 13 | Sodium Bicarbonate | 0.89 |
| 14 | Sodium Carbonate, Anhydrous | 1.43 |
| 15 | Poloxamer 407 | 1.79 |
| 16 | Palatinose | 2.50 |
| 17 | Propylene Glycol | 10.71 |
| | Total | 100.00 |

Method of Manufacture

The method for making the above example is the method of manufacture of Example 1.

Example VIII

A non-abrasive gel composition of the present invention contains the following components as described below:

| Item # | Material | % Comp. (w/w) |
|---|---|---|
| 1 | Glycerin | 88.64 |
| 2 | Xylitol | 5.00 |
| 3 | Polyethylene Glycol | 3.00 |
| 4 | Propylene Glycol | 3.00 |
| 5 | Fluoride | 0.24 |
| 6 | Flavor | 0.12 |
| | Total | 100.00 |

Method of Manufacture

The jacket temperature of a mixing tank is set to about 150° F. to about 160° F. Add glycerin, polyethylene glycol and propylene glycol to the mixing tank and agitate. Upon the temperature reaching approximately 120° F., add the xylitol, and fluoride. Mix for 30 minutes to form a homogeneous solution. Cool the tank to about 120° F., adding the flavoring agents and continue mixing for approximately 20 minutes. When permitted to cool, a gel product is formed.

Example IX

A mouth rinse composition of the present invention contains the following components as described below:

| Item # | Material | % Comp. (w/w) |
|---|---|---|
| 1 | USP Water | 65.60 |
| 2 | Sodium Lauryl Sulfate (27.9% Solution) | 0.75 |
| 3 | Polysorbate 80 | 0.20 |
| 4 | Glycerin | 5.00 |
| 5 | Propylene Glycol | 25.00 |
| 6 | Xylitol | 2.50 |
| 7 | Flavor | 0.12 |
| 8 | Fluoride | 0.24 |
| 9 | NaOH | 0.53 |
| 10 | Sodium Saccharin | 0.06 |
| | Total | 100.00 |

Method of Manufacture

Mix glycerin, polyethylene glycol and surfactants in the mixing tank at 160° C. for 30 minutes. Add water and mix for an additional 30 minutes. Upon reaching a temperature of about 120° F. Add the xylitol, fluoride, flavor and saccharin. Mix for 30 minutes to form a homogeneous solution. Cool the tank to about 120° F., adding the flavoring agents and continue mixing for approximately 20 minutes. Cool the tank to 40° C. and add NaOH to adjust pH to 6.8–7.2.

Example X

A mouth rinse composition of the present invention contains the following components as described below.

| Item # | Material | % Comp. (w/w) |
|---|---|---|
| 1 | USP Water | 58.10 |
| 2 | Sodium Lauryl Sulfate (27.9% Solution) | 0.75 |
| 3 | Polysorbate 80 | 0.20 |
| 4 | Glycerin | 5.00 |
| 5 | Propylene Glycol | 25.00 |
| 6 | Xylitol | 10.00 |
| 7 | Flavor | 0.12 |
| 8 | Fluoride | 0.24 |
| 9 | NaOH | 0.53 |
| 10 | Sodium Saccharin | 0.060 |
| | | Total 100.00 |

Method of Manufacture

The method for making the above example is the method of manufacture of Example IX.

Example XI

A mouth rinse composition of the present invention contains the following components as described below:

| Item # | Material | % Comp. (w/w) |
|---|---|---|
| 1 | USP Water | 85.50 |
| 2 | Sodium Lauryl Sulfate (27.9% Solution) | 0.75 |
| 3 | Polysorbate 80 | 0.20 |
| 4 | Glycerin | 10.00 |
| 5 | Butylene Glycol | 0.10 |
| 6 | Ribitol | 2.50 |
| 7 | Flavor | 0.12 |
| 8 | Fluoride | 0.24 |
| 9 | NaOH | 0.53 |
| 10 | Sodium Saccharin | 0.06 |
| | | Total 100.00 |

Method of Manufacture

The method for making the above example is the method of manufacture of Example IX.

Example XII

A mouth rinse composition of the present invention contains the following components as described below:

| Item # | Material | % Comp. (w/w) |
|---|---|---|
| 1 | USP Water | 78.00 |
| 2 | Sodium Lauryl Sulfate (27.9% Solution) | 0.75 |
| 3 | Polysorbate 80 | 0.20 |
| 4 | Glycerin | 10.00 |
| 5 | Hexylene Glycol | 0.10 |
| 6 | Melibiose | 10.00 |
| 7 | Flavor | 0.12 |
| 8 | Fluoride | 0.24 |
| 9 | NaOH | 0.53 |
| 10 | Sodium Saccharin | 0.06 |
| | | Total 100.00 |

Method of Manufacture

The method for making the above example is the method of manufacture of Example IX.

Example XIII

A liquid spray composition of the present invention contains the following components as described below.

| Item # | Material | % Comp. (w/w) |
|---|---|---|
| 1 | Xylitol | 10.00 |
| 2 | Polyethylene Glycol | 50.00 |
| 3 | Water | 9.20 |
| 4 | Cetylpyridinium Chloride | 0.04 |
| 5 | Propylene Carbonate | 30.00 |
| 6 | Sweetener[1] | 0.70 |
| 7 | Flavor | 0.04 |
| 8 | Color | 0.02 |
| | | Total 100.00 |

[1]Pro-Sweet Liquid K

Method of Manufacture

Mix cetylpyridinium chloride, flavors and colorant to the polyethylene glycol and propylene carbonate and mix for 1 hour or until homogenous. Add the water, xylitol, sweetener. Mix for 30 minutes to form a homogeneous solution and filter through a U.S. #100 mesh sieve. Fill into manually operated atomization pump and bottle. An example is manufactured by Calmar-Albert GmbH, the Mistette Mark II fitted with a 16 mm high viscosity head assembly which delivers 0.2 ml/actuation.

Example XIV

A liquid center lozenge composition of the present invention contains the following components as described below:

| Item # | Material | % Comp. (w/w) |
|---|---|---|
| 1 | Xylitol | 5.00 |
| 2 | Polyethylene Glycol 600 | 84.90 |
| 3 | Water | 5.00 |
| 4 | Cetylpyridinium Chloride | 0.05 |
| 5 | Propylene Glycol | 5.00 |
| 6 | Flavor | 0.04 |
| 7 | Color | 0.01 |
| | | Total 100.00 |

Method of Manufacture

Mix the cetylpyridinium chloride, flavors and colorant with the polyethylene glycol and propylene glycol. Continue mixing for 1 hour at about 30° C. or until homogenous. Add water and xylitol and mix for 30 minutes. Once homogeneous, filter through a U.S. #100 mesh sieve. Make individual filled lozenges containing about 1.0 ml of liquid per lozenge by a commonly used method such as extrusion.

Example XV

A gum composition of the present invention contains the following components as described below:

| Item # | Material | % Comp. (w/w) |
|---|---|---|
| 1 | Xylitol | 62.50 |
| 2 | Gum Base | 30.00 |
| 3 | Propylene glycol | 5.75 |
| 4 | Sodium Tartarate | 0.25 |
| 5 | Flavor | 1.49 |
| 6 | Color | 0.01 |
| | Total | 100.00 |

Method of Manufacture

Fully melt the gum base (at approximately 90° C.) in a jacketed mixer with sigma blades. Cool the gum base to about 70° C. and add propylene glycol. Mix until homogeneous. Cool this mixture to about 50° C. Add xylitol and mix until homogeneous. Cool mixture to about 35° C. and add the remaining ingredients. Remove mixture from kettle, roll to form a sheet of uniform thickness and score into gum sticks weighing about 2.5 g each.

We claim:

1. A method for treating and preventing caries by using on a routine basis an oral care composition consisting essentially of a safe and effective amount of xylitol and propylene glycol to improve uptake of said xylitol by plaque such that acid produced through plaque metabolism of sugars is sufficiently disrupted.

2. The method according to claim 1 wherein the oral care composition comprises from about 1% to about 65% by weight of the composition xylitol.

3. The method according to claim 2 wherein xylitol is from about 2.5% to about 20% by weight of the composition.

4. The method according to claim 3 wherein xylitol is from about 5% to about 10% by weight of the composition.

5. The method according to claim 1 wherein propylene glycol comprises from about 0.1% to about 50% by weight of the composition.

* * * * *